United States Patent [19]

Doss

[11] Patent Number: 4,679,561

[45] Date of Patent: Jul. 14, 1987

[54] IMPLANTABLE APPARATUS FOR LOCALIZED HEATING OF TISSUE

[75] Inventor: James D. Doss, Los Alamos, N. Mex.

[73] Assignee: The United States of America as represented by the United States Department of Energy, Washington, D.C.

[21] Appl. No.: 736,021

[22] Filed: May 20, 1985

[51] Int. Cl.⁴ .............................................. A61N 1/32
[52] U.S. Cl. .................................... 128/422; 128/401; 128/784; 128/804
[58] Field of Search ............... 128/804, 399, 401, 784, 128/419 C, 419 E, 419 R, 420 R, 420 A, 421, 422, 423 R, 736; 374/122, 121

[56] References Cited

U.S. PATENT DOCUMENTS

| | | |
|---|---|---|
| 3,796,221 | 3/1974 | Hagfors ................................ 128/421 |
| 4,016,886 | 4/1977 | Doss et al. . |
| 4,095,602 | 6/1978 | LeVeen ........................... 128/422 X |
| 4,154,246 | 5/1979 | LeVeen . |
| 4,186,729 | 2/1980 | Harrison . |
| 4,346,715 | 8/1982 | Gammell . |
| 4,378,806 | 4/1983 | Henley-Cohn . |
| 4,397,314 | 8/1983 | Vaguine . |
| 4,448,198 | 5/1984 | Turner . |

FOREIGN PATENT DOCUMENTS

84/02839 8/1984 PCT Int'l Appl. ................. 128/736

Primary Examiner—Lee S. Cohen
Attorney, Agent, or Firm—Samuel M. Freund; Ray G. Wilson; Judson R. Hightower

[57] ABSTRACT

With the object of repetitively treating deep-seated, inoperable tumors by hyperthermia as well as locally heating other internal tissue masses repetitively, a receiving antenna, transmission line, and electrode arrangment are implanted completely within the patient's body, with the receiving antenna just under the surface of the skin and with the electrode arrangement being located so as to most effectively heat the tissue to be treated. An external, transmitting antenna, driven by an external radio-frequency energy source, is closely coupled to the implanted receiving antenna so that the energy coupled across the air-skin interface provides electromagnetic energy suitable for heating the tissue in the vicinity of the implanted electrodes. The resulting increase in tissue temperature may be estimated by an indirect measurement of the decrease in tissue resistivity in the heated region. This change in resistivity appears as a change in the loading of the receiving antenna which can be measured by either determining the change in the phase relationship between the voltage and the current appearing on the transmitting antenna or by measuring the change in the magnitude of the impedance thereof. Optionally, multiple electrode arrays may be activated or inactivated by the application of magnetic fields to operate implanted magnetic reed switches.

6 Claims, 5 Drawing Figures

IMPLANTABLE APPARATUS FOR LOCALIZED HEATING OF TISSUE

This invention is the result of a contract with the Department of Energy (Contract No. W-7405-ENG-36).

BACKGROUND OF THE INVENTION

The present invention relates generally to hyperthermia and, more particularly, to the use of electrodes internally placed in the vicinity of or inside of tissue to be heated in cooperation with an internally located receiver of radio-frequency energy for actuating pairs of electrodes, whereby an electric current flows between a particular pair of electrodes in such a manner that the tissue therebetween is heated and the temperature therein may be simultaneously automatically monitored during the procedure.

It is well known that elevating the temperature of tumors is helpful for reducing their size and tendency for metastasis. Modalities for applying heat to tumors include the use of direct contact radio-frequency (rf) applicators, microwave radiation, inductively coupled radio-frequency fields, ultrasound, and a variety of simple thermal conduction techniques.

Among the problems associated with all of these procedures is the requirement that highly localized heat be produced at depths of several centimeters beneath the surface of the body. Techniques have been developed whereby microwave radiation and ultrasound may be focused at various desired depths and radio-frequency applicators may be used at depth during surgery. However, the degree of localization is generally poor with the result that healthy tissue may be harmed. Induction heating gives rise to poor localization of the incident energy as well. That is, although induction heating may be achieved by placing an antenna on the surface of the body, superficial eddy currents are generated in the immediate vicinity of the antenna when it is driven using rf current, and unwanted surface heating occurs with little coupling to the underlying tissue. Thus, the currently employed, noninvasive procedures for providing heat to internal tumors, are incapable of doing so that substantial specificity and selectivity.

Another difficulty which arises as a result of the use of the above-described non-invasive techniques is the difficulty in the determination of the temperature of the heated tissues. Temperature awareness and control is of extreme importance during the administration of hyperthermia to internal body tissue since there is merely a small range of temperature which separates the destruction of tumor cells from the destruction of healthy tissue. Thermocouples and thermistors are commonly used to measure the temperature of the treated tissue, but they must be inserted into the vicinity of the tissue itself in order to produce accurate measurements, a process which may be traumatic to the patient.

Yet another problem with existing hyperthermia procedures arises if the patient requires more than one application of the procedure. This is often the case since many tumors can only be partially removed by surgical methods, and generally only temporary remission or tumor shrinkage results from a single hyperthermia treatment. Repeated applications would necessarily require surgery unless electrical leads are placed so as to emerge through the skin. The former situation might be at most repeated once or twice for a seriously ill patient if the tumor is located within a major body cavity, while the latter situation presents a significant risk of infection.

In "Method for Localized Heating in Tumor Tissue," U.S. Pat. No. 4,016,886, issued to Doss et al. on Apr. 12, 1977, the inventors describe a method for localized heating of tissue using radio-frequency currents applied directly to an exposed tumor which is effective only during the time that the tumor is accessible. This difficulty is partially solved according to the teachings of U.S. Pat. No. 4,448,198, "Invasive Hyperthermia Apparatus and Method," issued to Paul F. Turner on May 15, 1984. Therein the inventors describe the use of a plurality of needle-like electromagnetic energy applicators adapted for insertion into body tissue and radiating electromagnetic energy therein. A similar technique is described in U.S. Pat. No. 4,346,715, "Hyperthermia Heating apparatus," issued to Paul M. Gammell on Aug. 31, 1982. Although the latter two patents teach procedures which may be repeatedly used without exposing the tumor, risk of infection and healthy tissue damage remain ever present.

In "Method and Apparatus for Controlling and Optimizing the Heating Pattern for a Hyperthermia System," U.S. Pat. No. 4,397,314, issued to Victor A. Vaguine on Aug. 9, 1983, "Gapped Resonant Microwave Apparatus for Producing Hyperthermia Therapy of Tumors," U.S. Pat. No. 4,378,806, issued to Julian L. Henley-Cohn on Apr. 5, 1983, and "Deep Heating Electrode," U.S. Pat. No. 4,186,729, issued to William H. Harrison on Feb. 5, 1980, procedures are taught for the noninvasive heating of living tissue. However, there is little localization of the radiation and invasive temperature measurements are necessry to insure that healthy tissue is not heated excessively.

In "field Intensification in Radio Frequency Thermotherapy," U.S. Pat. No. 4,154,246, issued to Harry H. LeVeen on May 15, 1979, the inventor describes a tuned radio-frequency inductance element which may be implanted into the region of the tissue to be heated or inserted into any conveniently accessible tubular organ close thereto for intensifying the electromagnetic radiation impinging thereon supplied from an external source of such radiation which would otherwise be poorly directed and localized. There are no teachings therein of means for coupling the energy in the radio-frequency radiation impressed upon the implanted closed, resonant inductive circuit to the tissue to be heated. Indeed, the inventor has deliberately sought to minimize heating losses in the inductor by using copper or silver-coated copper as the inductor material. Moreover, there is no electrical contact between the resonant loop and the tissue since the implanted device is insulated. Therefore, any voltages generated thereon will not cause currents to flow in the adjacent tissue. Finally, the inductance element in LeVeen's patent may be buried deep within the body of the patient and consequently at a significant distance from the external source of radiation. That is, LeVeen does not teach close coupling between the external electromagnetic radiation source and the internally positioned closed resonant circuit.

Clearly then, an improved hyperthermia treatment of tumors would involve a noninvasive, well-localized procedure for heating tumors with specificity and temperature control. In the absence of suitable noninvasive procedures and the likelihood that the treatment will have to be repeated, an effective internally placed device would simplify the treatment and minimize the potential for infection.

Accordingly, an object of the present invention is to provide an apparatus for repeatedly heating tissue internal to a patient, locally and with significant specificity.

Another object of my invention is to provide an apparatus for repeatedly heating tissue internal to a patient, locally and with significant specificity without the danger thereto accompanying repeated surgical procedures to access the tissue to be heated, and without significant risk of infection and discomfort which accompanies the use of externally powered electrodes which must be inserted through the skin to apply radio-frequency energy to the tissue.

Yet another object of my invention is to provide an apparatus for the noninvasive measurement of the temperature of the tissue under treatment and for the control of the temperature therein.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the apparatus of this invention includes a radio-frequency source coupled to an antenna located externally to the patient, a subcutaneous antenna for receiving the radio-frequency radiation and having an electrical connection for coupling the energy transferred thereto out of the internally located antenna, internally located electrodes in electrical contact with the electrical connection of the internally located antenna and inserted into the tissue to be heated, and external means for measuring the temperature of the heated tissue. Preferably, the apparatus of the present invention includes means for measuring changes in the phase relationship between the voltage impressed onto the external antenna by the radio-frequency source and the resulting current generated therein, the phase change measured thereby being related to the temperature changes in the tissue.

Benefits and advantages of my invention include the ability to repeatedly heat specific tissue located internally to a patient without having to repeatedly expose the tissue by surgical techniques and without the risk of infection and patient discomfort resulting from the repeated insertion of electrodes into the tissue through the skin prior to treatment. Moreover, according to the practice of the present invention, temperature measurements can be made on the tissue under treatment in a noninvasive manner.

BRIEF DESCRIPTION OF THE DRAWINGS

The accompanying drawings, which are incorporated in and form a part of the specification, illustrate two embodiments of the present invention and, together with the description, serve to explain the principles of the invention. In the drawings.

DETAILED DESCRIPTION OF THE INVENTION

Briefly, in its simplest form, the apparatus of the present invention includes a transmitting antenna, located externally to the patient to be treated and powered by a source of radio-frequency radiation, a receiving antenna surgically placed subcutaneously inside of the patient, but in a location such that close coupling between the two antennas can be achieved, and a plurality of electrodes embedded in the tissue to be heated and connected to the receiving antenna using a transmission line so that voltages generated thereon as a result of the interaction of the receiving antenna with the transmitting antenna can produce currents in the tissue. Changes in the voltage and current characteristics of the transmitting antenna can be used to indirectly monitor the temperature of the tissue since these characteristics are sensitive to the loading on the receiving antenna.

Figure 1:
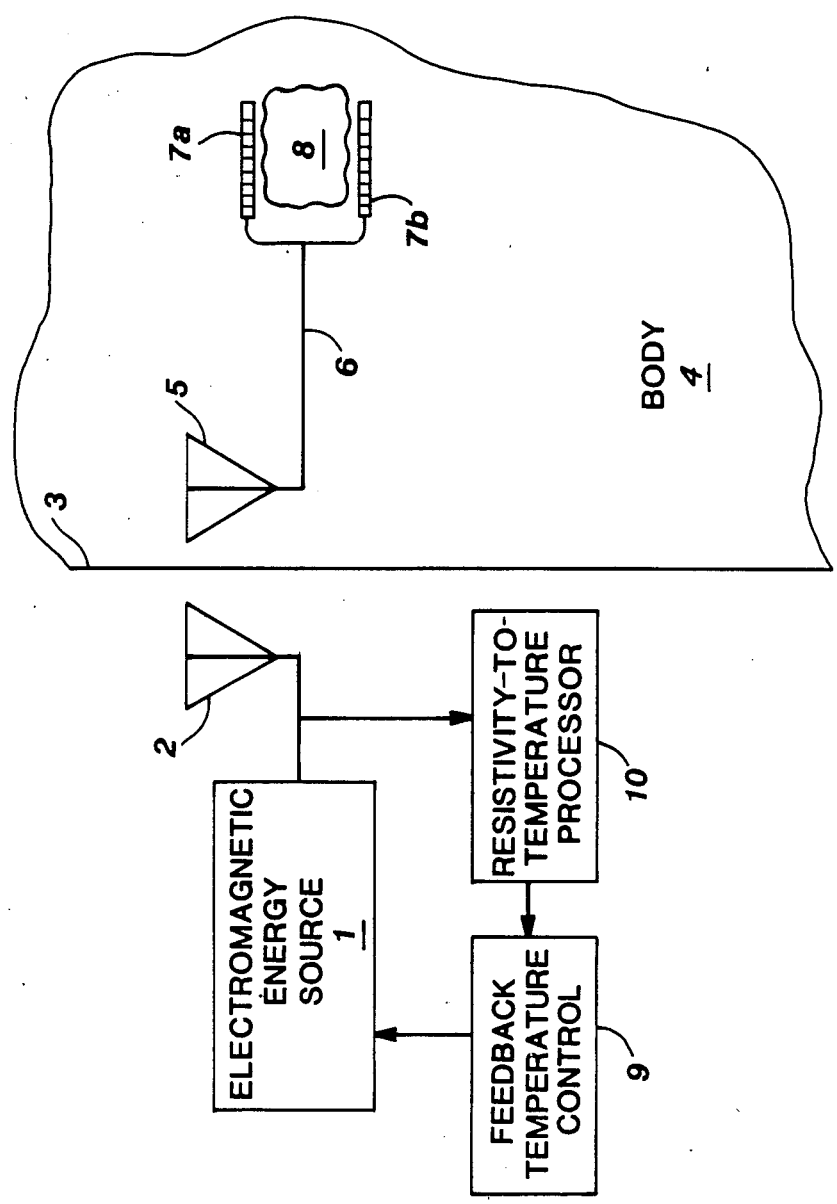
FIG. 1 is a schematic representation of the apparatus of the present invention showing the most general configuration thereof where a simple external transmitting antenna is closely coupled to a subcutaneously placed receiving antenna and the temperature of the heated tissue is indirectly sensed, thereby permitting the power level supplied to the transmitting antenna to be controlled.

Reference will now be made in detail to two present preferred embodiments of the invention, an example of each of which is shown in the accompanying drawings. Identical numbers are used throughout to described similar or identical elements of the present invention. Turning now to the drawings, FIG. 1 shows a schematic representation of a general embodiment of the present invention. An electromagnetic energy source 1 is used to power transmitting antenna 2 which transmits electromagnetic energy through the skin boundary layer 3 of the patient's body 4. This energy is received by closely coupled, subcutaneously implanted antenna 5 and transmitted along transmission line 6 to electrode 7a, 7b which are located in the vicinity of tissue mass 8 which is intended to be repetitively heated.

As tissue mass 8 is heated by the action of the current flow therein, its temperature increases which results in a decrease of electrical resistivity thereof. This reduction in resistivity results in a reduction in the load impedance of implanted antenna 5 causing a change in the load impedance of closely coupled transmitting antenna 2, with a corresponding decrease in the observable ratio of voltage to electric current appearing on transmitting antenna 2. The phase relationship between the voltage and current on transmitting antenna 2 is also affected by changes in loading of implanted antenna 5. The measured change in the ratio of voltage to current or the change in the phase relationship between these two parameters on transmitting antenna 2 can then be converted to a change in tissue temperature by processing means 10. This information can also yield the actual temperature of tissue mass 8 if the pretreatment temperature thereof is known. The temperature information can be directed to an automatic feedback circuit 9 in order to adjust the temperature in tissue mass 8 to a preset level and maintain it at this temperature by controlling the power level from external electromagnetic energy source 1.

Figure 2:
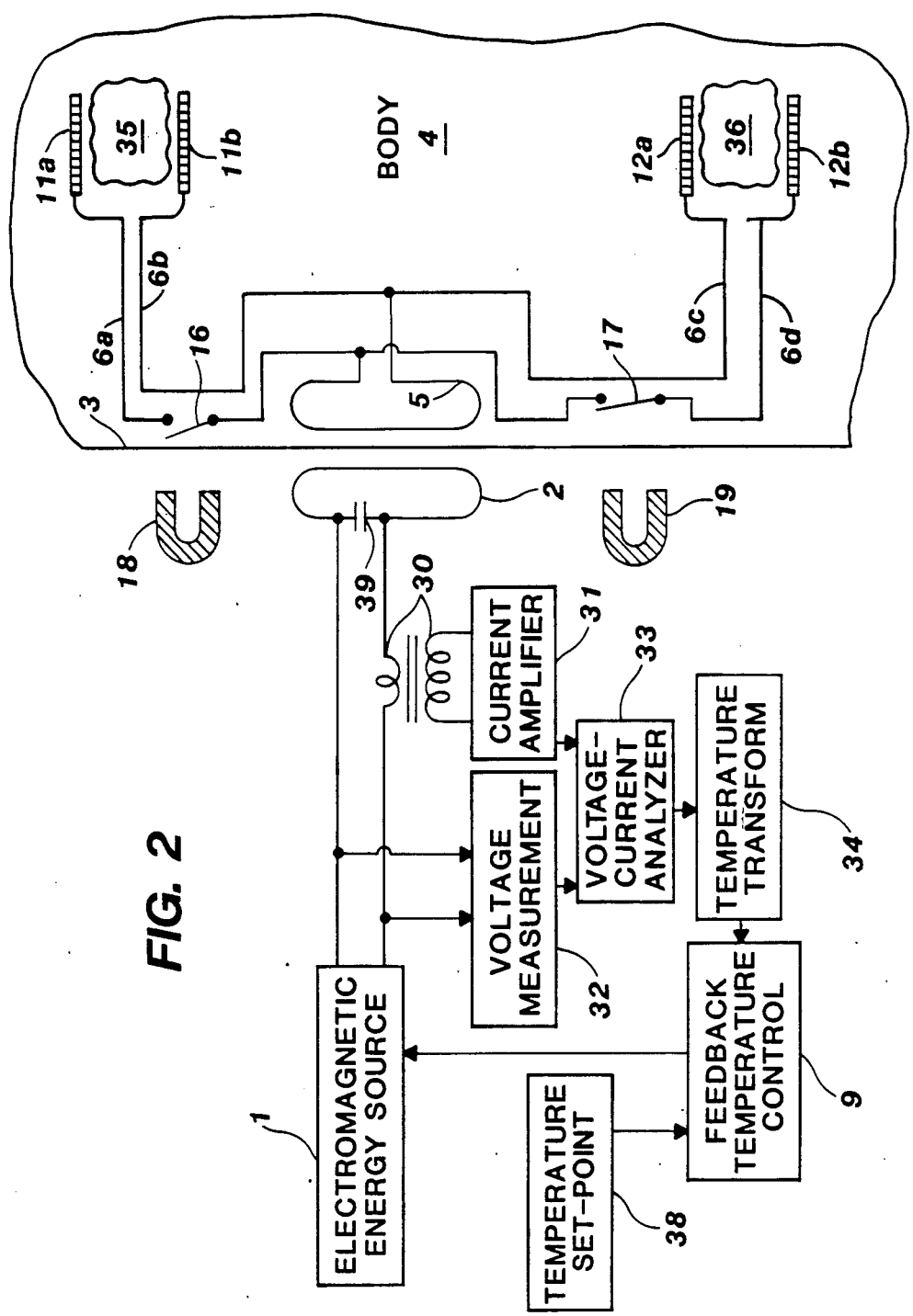
FIG. 2 is a more detailed schematic representation of the apparatus of my invention showing voltage and current amplitude measurement apparatus connected to the transmitting antenna for the purpose of indirect determination of the tissue temperature and the control thereof by a temperature feedback controller.

FIG. 2 shows a more detailed schematic representation of the general apparatus depicted in FIG. 1, described hereinabove, illustrating the operation of multiple electrode assemblies deriving energy from a single implanted magnetic loop antenna 5. Magnetic reed switches 16, 17 may be utilized to direct energy to either or both of the electrode assemblies 11a, 11b and 12a, 12b through transmission lines 6a, 6b and 6c, 6d, respectively, which heat tissue masses 35 36, respectively. Shown in FIG. 2 is the use of series connected, normally open magnetic reed switches 16 and 17, operated by external magnetic fields applied thereto, for example, by the proximate placement of external magnets 18 and 19. The implanted magnetic reed switches are shown in switch positions that would prevent significant power from being applied to either electrode assembly 11 or 12 even if closely coupled transmitting antenna 2 were in place and active. Also shown in FIG. 2 is the use of a magnetic loop transmitting antenna. Voltage and current measurement and processing means 10, illustrated in FIG. 1 is shown in more detail as including current transformer 30, which drives current amplifier 31, and voltage measurement means 32. Voltage-current analyzer 33 would be then utilized to either provide the ratio of the voltage to the current appearing on transmitting antenna 2, which is proportional to the resistive load thereon, in one embodiment of my invention, or to provide the phase relationship between the voltage and the current thereon in a second embodiment thereof. Temperature transform means 34 could include a digital microprocessor to perform the transformations of the voltage and current measurements to tissue temperature information. The temperature transform means 34 drives feedback temperature control means 9 which controls the temperature in either or both of tissue masses 35 and 36 by adjusting the power output of electromagnetic energy source 1. Generally, only one of the electrode assemblies 11a, 11b, 12a, 12b would be energized at a given time. The desired control temperature is determined by temperature set-point means 38.

Figure 3:
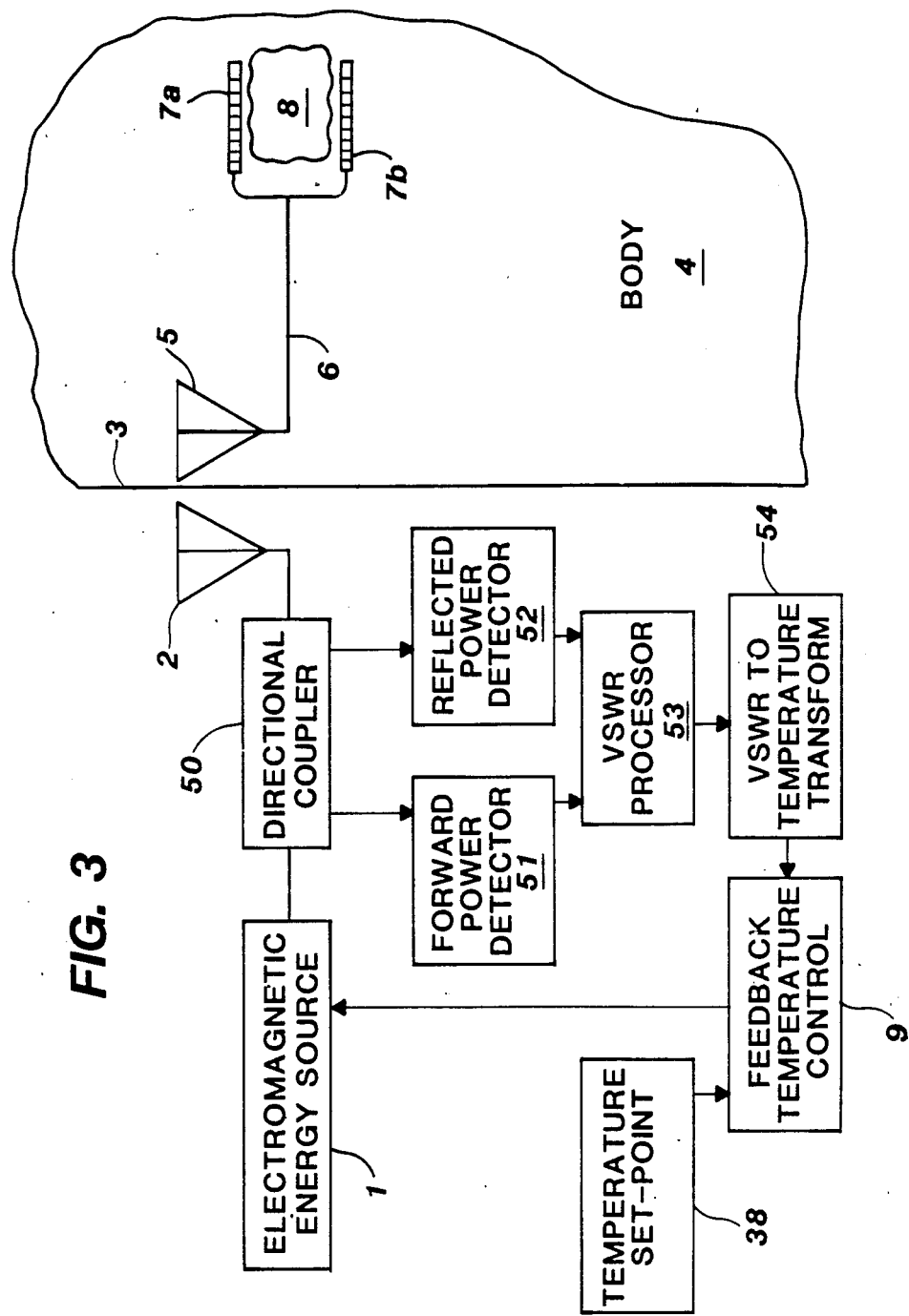
FIG. 3 is a more detailed schematic representation of another embodiment of my invention showing apparatus for determining changes in the power transferred from the transmitting antenna to the internally placed receiving antenna for the purpose of indirect determination of the tissue temperature and the control thereof by a temperature feedback controller.

FIG. 3 is a schematic representation of another preferred embodiment of the apparatus of the present invention. In this embodiment, changes in the temperature of tissue mass 8 are indirectly determined by measuring the quantity of power transferred from the transmitting antenna 2 to the receiving antenna 5. This is accomplished using directional coupler 50 which is interposed in electrical contact between the electromagnetic energy source 1 and receiving antenna 2. Power directed to antenna 2 and power reflected therefrom is measured by detectors 51 and 52, respectively, processed by processor 53 and converted into a value of the temperature by transformer 54 which can be used in the feedback system described in FIG. 2 to control the temperature to which the heated tissue is brought to.

It should be mentioned at this point that the precise configuration of the electrode assembly will be a function of specific anatomy involved as well as the size and shape of the particular malignancy to be treated. Details of the electrode design are not critical to the present invention. While the electrodes may be constructed with arrays of pins, for the purpose of understanding the present invention, one may consider a simple electrode configuration, such as two parallel conducting plates. Once the antenna/transmission line/electrode assembly (receiving circuitry) is surgically installed, the specified tissue volume may be heated as often as desired by coupling an external source of electromagnetic energy to the implanted antenna.

Figure 4:
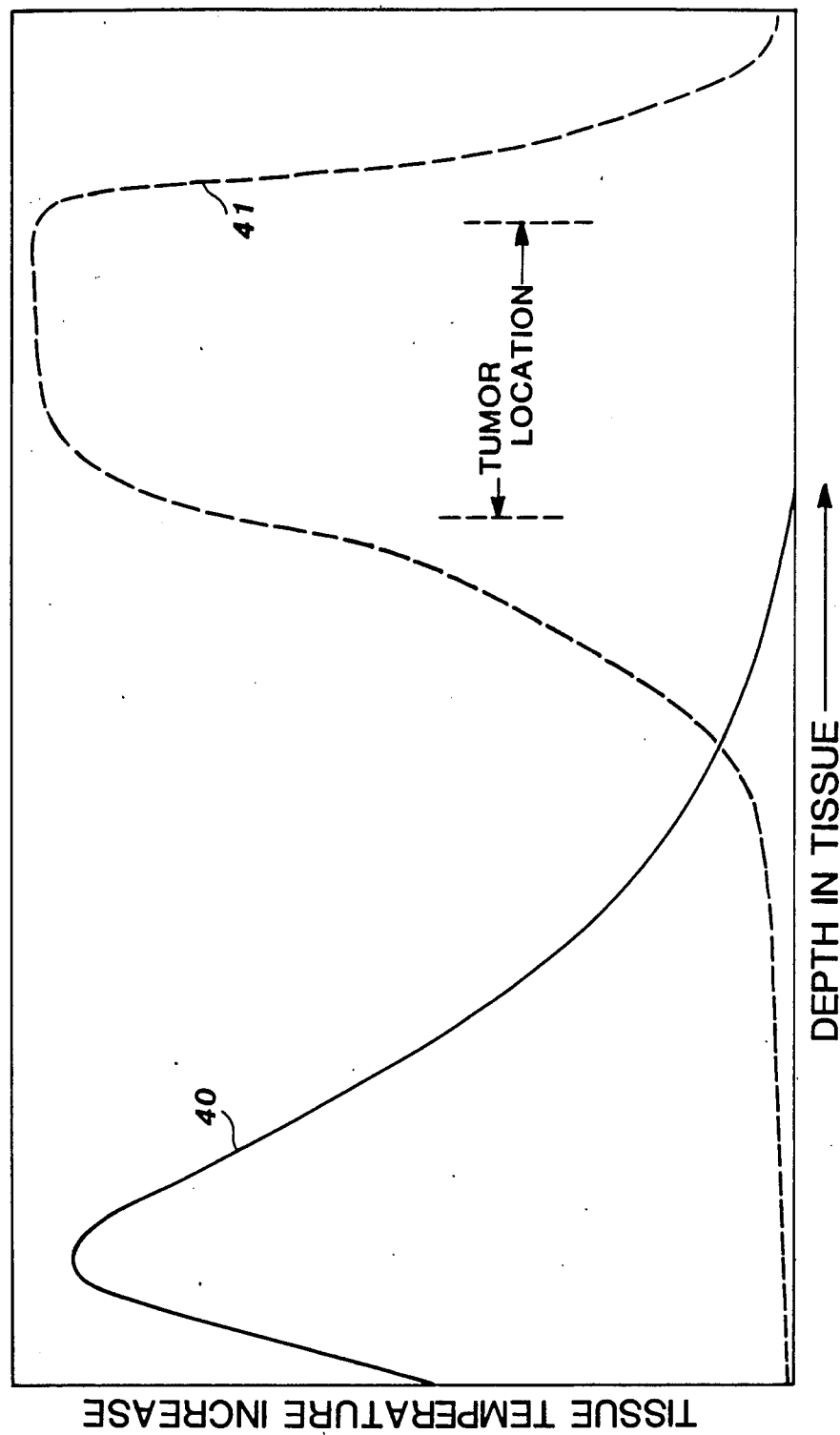
FIG. 4 shows a comparison of the temperature distribution in tissue deriving from external irradiation by radio-frequency radiation and from the apparatus of the present invention for tumors located internally away from the surface of the skin.

FIG. 4 shows a representative graph, based upon both calculations and measurements, illustrating some of the advantages of the present invention over conventional inductive heating techniques where deep, highly localized heating is required. Curve 40 represents the temperature distribution in irradiated tissue obtained by conventional inductive or microwave heating and illustrates that heat is deposited near the surface of the patient's body, such energy deposition being inappropriate for the heating of tissue deeply embedded within the body. Curve 41, by contrast, illustrates how a particular temperature distribution may be highly localized in depth according to the practice of the present invention.

Having generally described the invention, the following example is given as a further illustration thereof.

EXAMPLE

Figure 5:
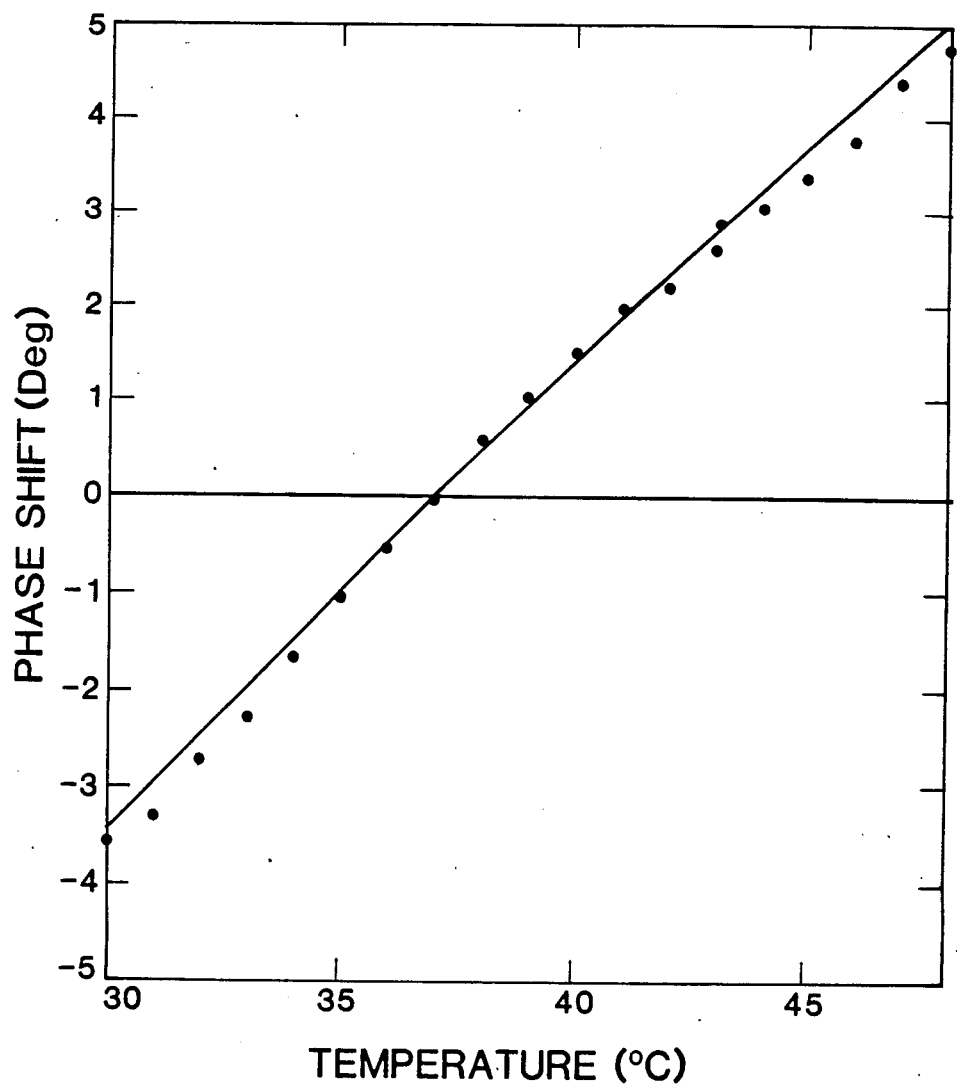
FIG. 5 shows a graph of the phase relationship between the voltage and the current appearing on the external transmitting antenna as a function of the temperature experienced by a material having very similar conductivity and other electrical characteristics to that of human tissue in which electrodes attached to the receiving antenna are located.

One procedure for determining the temperature of the heated tissue derives from the observation that the phase relationship between the voltage and the current appearing on the transmitting antenna 2 is affected by the resistivity experienced by the electrodes 7a, 7b implanted in the tissue to be heated 8 which are in turn connected to receiving antenna 5, as shwon in FIG. 1. FIG. 5 is derived from an apparatus similar to that represented in FIG. 2, wherein the receiving antenna is submerged in a melted saline gel having a resistivity approximately equivalent to muscle tissue. The solid curve represents the results calculated from a theoretical model describing the experiment of the Example while the dots represent actual measurements. Instead of analyzing the ratio of the magnitudes of the external voltage and current appearing on the transmitting antenna, the phase relationship is measured as a function of the temperature of the gel sample. Temperature changes about a core temperature fiducial point have been observed with an accuracy of about 0.25° C. by this procedure and it is expected that refinements will produce much greater accuracy.

It should be mentioned that in order to make optimum use of the phase angle between the voltage and the current on the external antenna to determine the change in load on the implanted antenna which can be related to the change in temperature of the heated tissue, the transmitter apparatus should be "tuned" to a frequency below that supplied by the radio-frequency generator. That is, if the radio-frequency generator of the present invention is chosen to operate at 13.56 MHz, the external transmitter circuitry which receives this input must be resonant for lower frequencies, say 13.0 MHz. The tuning is accomplished by choosing the appropriate value for tuning capacitor 39 shown in FIG. 2. In this manner, the phase relationship varies monotonically with the temperature of the tissue. Conversely, if one uses the magnitude of the measured impedance of the external antenna to determine the change in the tissue temperature, it is preferable that the transmitter should be tuned to the same or higher frequencies. That is, for the radio-frequency generator supplied frequency of 13.56 MHz, the external transmitter circuitry can be operated from, say, 13.56 to 13.8 MHz. At lower frequencies, the magnitude of the impedance change with implanted receiving antenna loading and consequently with changes in the tissue temperature may not be sufficient for the purposes of the present invention.

The foregoing description of three preferred embodiments of the invention has been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What I claim is:

1. An apparatus for locally increasing the temperature of living tissue located inside of a body, said apparatus comprising in combination:
   a. means disposed externally to the body for generating radio-frequency electromagnetic energy having a chosen intensity;
   b. first antenna means for receiving and for radiating the radio-frequency electromagnetic energy from said means for generating radio-frequency electromagnetic energy, said first antenna means being adapted for placement at substantially the closest location external to the body to the tissue to be heated;
   c. second antenna means closely coupled to said first antenna means for receiving the radiated electromagnetic energy and for generating an alternating voltage therefrom having a first electrical connection and a second electrical connection, said second antenna means being adapted for location within the body near an accessible outer surface thereof in order to facilitate receiving the radiated electromagnetic energy, whereby the alternating voltage appears between said first electrical connection and said second electrical connection;
   d. at least one first electrode means being in electrical contact with said first electrical connection and at least one second electrode means being in electrical contact with said second electrical connection for receiving the alternating voltage appearing between said first electrical connection and said second electrical connection of said second antenna means, said at least one first electrode means and said at least one second electrode means being adapted for location within the tissue to be heated in the vicinity of at least one of said first electrode means and said second electrode means causing thereby an increase in temperature therein; and
   e. means for externally measuring the voltage current characteristics of said first antenna means for determining the increase in temperature within the tissue to be heated, said means for externally measuring the voltage current characteristics of said first antenna means having parametric dependence on the change in electrical resistance within the tissue to be heated resulting from the increase in temperature therein.

2. The apparatus as described in claim 1, wherein said external temperature determining means includes a directional coupler located in between said radio-frequency electromagnetic energy generation means and said first antenna means, said directional coupler having a first output for sampling the output from said radio-frequency electromagnetic energy generation means and a second output for sampling reflected power from said first antenna means.

3. The apparatus as described in claim 1, wherein said external temperature determining means includes means for measuring the voltage appearing across said first antenna means, means for measuring the current passing through said first antenna means, and means for receiving the voltage and the current so measured and for relating the voltage and current measured thereby to the temperature increase in the tissue to be heated.

4. The apparatus as described in claim 3, wherein said means for receiving and for relating the voltage and current relates changes in the phase shift between the voltage and the current measured thereby to the temperature increase in the tissue to be heated.

5. The apparatus as described in claim 3, wherein said means for receiving and for relating the voltage and current relates the ratio of the voltage and the current measured thereby to the temperature increase in the tissue to be heated.

6. The apparatus as described in claims 4 or 5, wherein means are provided for controlling the temperature of the tissue to be heated by adjusting the intensity of said means for generating radio-frequency electromagnetic energy, said temperature controlling means having as its input the output of the means for receiving and for relating the voltage and the current.

* * * * *